United States Patent
Minogue

[19]

[11] Patent Number: 6,134,480
[45] Date of Patent: Oct. 17, 2000

[54] ELECTRODE ASSEMBLY

[75] Inventor: Conor Minogue, Kinvara, Ireland

[73] Assignee: BMR Research & Development Limited, County Donegal, Ireland

[21] Appl. No.: 08/816,843

[22] Filed: Mar. 13, 1997

[30] Foreign Application Priority Data

Mar. 15, 1996 [IE] Ireland ..................................... 960224

[51] Int. Cl.[7] ............................ A61B 5/0408; A61N 1/04
[52] U.S. Cl. ......................... 607/152; 600/391; 600/393; 600/395
[58] Field of Search ................................... 600/382–384, 600/391–394, 386, 395; 607/152

[56] References Cited

U.S. PATENT DOCUMENTS

| | | | |
|---|---|---|---|
| 3,993,049 | 11/1976 | Kater | 600/391 |
| 4,687,004 | 8/1987 | Zenkich | 128/798 |
| 4,777,954 | 10/1988 | Keusch et al. | 128/640 |
| 4,926,878 | 5/1990 | Snedeker et al. | 607/152 |
| 5,255,677 | 10/1993 | Schaefer et al. | 607/152 |
| 5,354,321 | 10/1994 | Berger | 607/152 X |
| 5,496,363 | 3/1996 | Burgio et al. | 617/152 |
| 5,678,545 | 10/1997 | Stratbucker | 600/382 |
| 5,938,597 | 8/1999 | Stratbucker | 600/382 |

FOREIGN PATENT DOCUMENTS 0284943  10/1988  European Pat. Off. ............... 128/640

*Primary Examiner*—Jeffrey R. Jastrzab
*Attorney, Agent, or Firm*—Woodcock Washburn Kurtz Mackiewicz & Norris LLP

[57] ABSTRACT

An electrode assembly for application to a patient's skin comprises an electrically insulating substrate 13 bearing at least two spaced apart electrodes 18, and an electrically conductive layer 14 on the substrate which covers the electrodes and which in use of the assembly is applied to the patient's skin. The electrical impedence of the region of the layer 14 overlying each electrode 18 is less than the electrical impedence between the electrodes laterally through the layer.

5 Claims, 3 Drawing Sheets

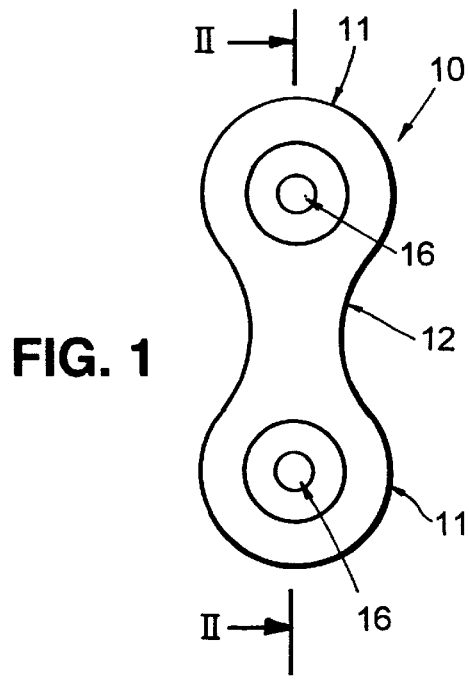
FIG. 1
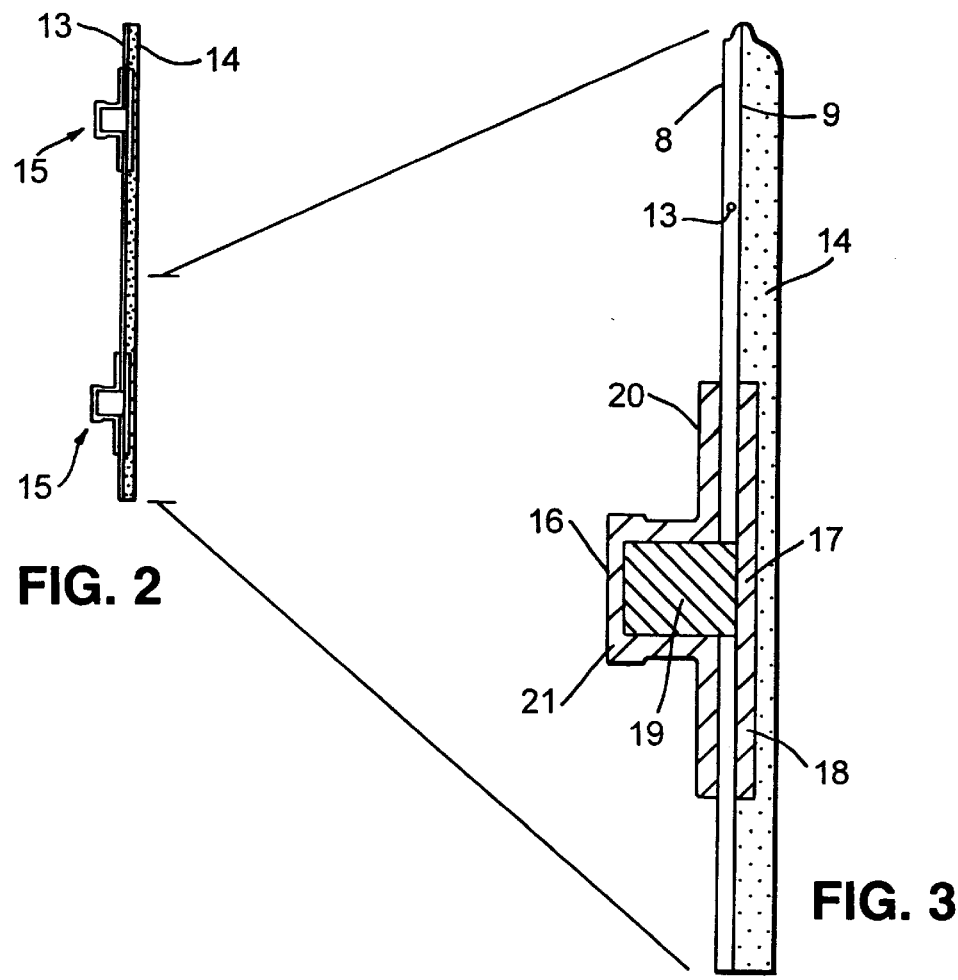
FIG. 2
FIG. 3

ELECTRODE ASSEMBLY

The present invention relates to an electrode assembly. In particular, the invention relates to an electrode assembly which is, in use, applied to a patient's skin and through which trans-epidermal muscle stimulation can be administered.

According to the present invention there is provided an electrode assembly for application to a patient's skin, comprising an electrically insulating substrate bearing at least two spaced apart electrodes, and an electrically conductive layer on the substrate which covers the electrodes and which in use of the assembly is applied to the patient's skin, the electrical impedance through the thickness of the layer in the region overlying each electrode being less than the electrical impedance between the electrodes laterally through the layer.

An embodiment of the invention will now be described, by way of example, with reference to the accompanying drawings, in which:

FIG. 1 is a plan view of an electrode assembly according to the embodiment;

FIG. 2 is a cross-sectional view of the electrode assembly of FIG. 1 taken through the line II—II;

FIG. 3 is a more detailed cross-sectional view of the electrode construction in the assembly of FIG. 2;

Figure 4:
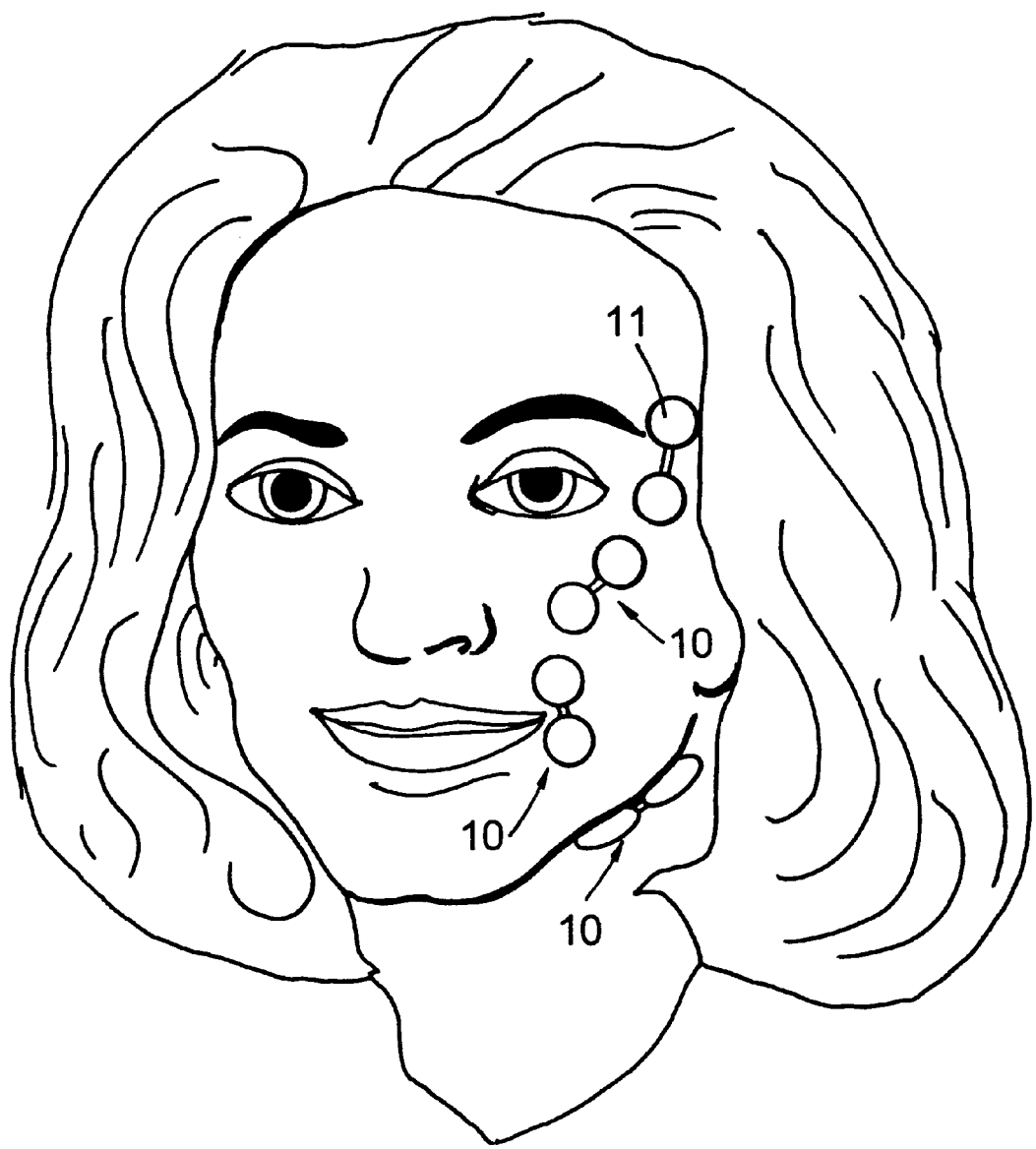
FIG. 4 illustrates a plurality of electrode assemblies according to the embodiment in use.

Referring to the drawings, an electrode assembly 10 comprises a figure-of-eight-shaped substrate 13 having enlarged substantially circular ends 11 connected by a narrow waist portion 12. The substrate 13 is made of an electrically insulating material and has front and rear surfaces 8, 9 respectively.

Two substantially circular electrodes 18 are provided on the rear surface 9 of the substrate 13, each substantially concentric with a respective enlarged end 11. Each such electrode is, in this embodiment, constituted by the circular base 18 of the male part 17 of a standard dot snapper 15 comprising inter-engaging metal female and male parts 16 and 17 respectively.

A hole (not shown) is formed centrally in each enlarged end 11 of the substrate 13. Each male part 17 of the dot snapper 15 comprises the circular base (electrode) 18 having a diameter greater than the diameter of the holes formed in the substrate 13, and a stud 19 projecting from the base 18 through a respective hole in the substrate 13 so as to project beyond the front surface 8 of the substrate. Each female part 16 comprises an annular base 20, approximately equal in diameter to the electrode 18, and a cylindrical socket 21 which is in snap engagement with the stud 19. The part of the substrate 13 surrounding each hole is sandwiched between the electrode 18 located on the rear surface 9 and the base 20 located on the front surface 8, thus fixing the dot snappers 15, and hence the electrodes 18, in place on the substrate 13.

An electrically conductive layer in the form of a continuous hydrogel layer 14 is applied to substantially the entire rear surface 9 of the substrate 13, covering the electrodes 18.

In use, the electrode assembly 10 is applied to a patient with the exposed surface of the hydrogel layer 14 in contact with the patient's skin. Electrical signals are applied to the patient via the electrodes 18 from a muscle stimulator apparatus (not shown) which is connected to the sockets 21 on the front surface 8 of the substrate 13.

The electrical impedence through the thickness of the hydrogel layer 14 in the region overlying each electrode 18, i.e. the region which in use of the assembly 10 is between the electrode and the patient's skin, is very much less than the electrical impedence of the hydrogel layer between the electrodes 18. This is because the electrical signals travel a relatively short distance through the thickness of the hydrogel layer 14 from each electrode 18 to the patient's skin in comparison to the lateral distance along the hydrogel layer 14 between the electrodes 18. Since the impedence between the electrodes 18 through the patient's skin is lower than the impedence of the hydrogel layer 14 between the electrodes, the continuous hydrogel layer 14 does not present a short-circuit between the two electrodes 18.

The electrode assembly 10 is particularly useful in the application of trans-epidermal muscle stimulation to a patients facial muscles, as shown by some of the possible in-use positions of the electrode assembly in FIG. 4.

Figure 5:
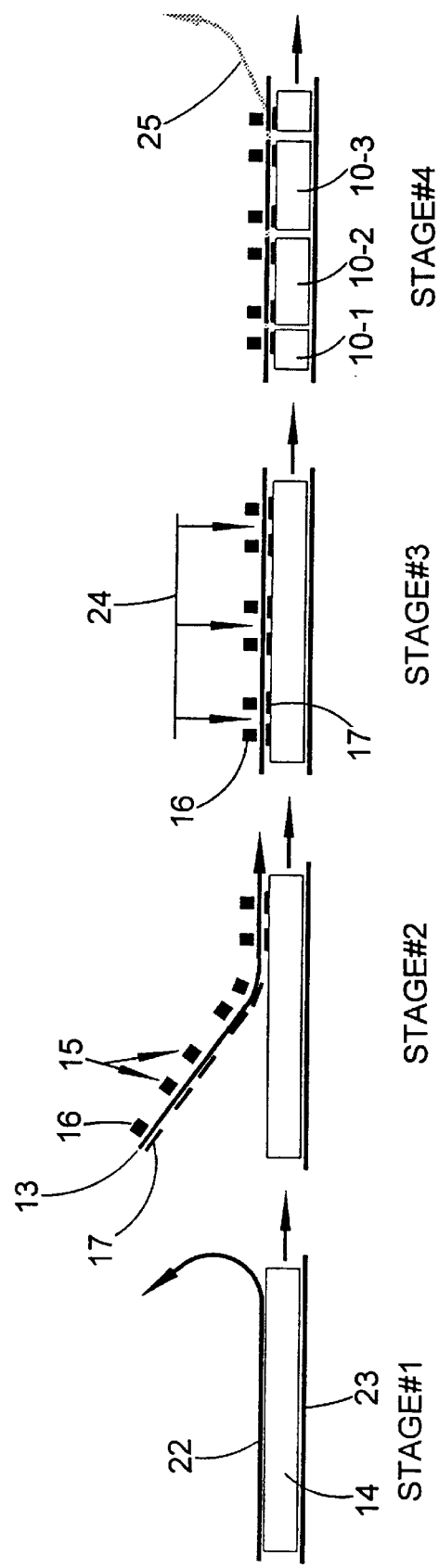
FIG. 5 is a schematic illustration of a fabrication process for electrode assemblies according to the embodiment.

Electrode assemblies 10 can be fabricated in a continuous process as shown in FIG. 5 which shows the four main stages, Stages #1 to #4, of the process. Hydrogel 14 is supplied to the process at Stage #1 in a continuous layer sandwiched between upper and lower acetate sheets 22, 23 respectively. The upper sheet 22 is removed during Stage #1 before the exposed hydrogel layer 14 is fed to Stage #2 where substrate material 13, pre-populated with dot snappers 15, is applied to the exposed surface of the hydrogel layer 14. The continuous laminate 13/14/23 is then fed to Stage #3 where a punch 24 is used to cut figure-of-eight shaped outlines from the substrate 13 and hydrogel layer 14, each including two dot snappers 15, to define a plurality of electrode assemblies 10-1, 10-2, 10-3, etc. The punch 24 does not penetrate the lower sheet 23 because it is the sheet 23 which is used to draw the hydrogel 14 and pre-populated substrate 13 through the various stages of the process.

In Stage #4, waste material 25, which is preferably in the form of a continuous sheet of substrate material and hydrogel, is removed to leave discrete electrode assemblies 10-1, 10-2, 10-3, etc., on the sheet 23. These electrode assemblies 10 can then be removed from the sheet 23 and packed for shipping as required. It will be seen that the substrate material 13 can be pre-populated in such a pattern and the punch 24 so shaped that a minimum of waste material is produced.

The provision of multiple electrodes on each electrode assembly simplifies the manufacture of the electrode assemblies as compared to manufacturing individual electrodes, as well as providing a greater surface area and hence greater adhesion to the patient's skin than if discrete small area electrodes were used. Also, a twin core lead wire can be used to make contact to the assembly; where separate electrodes for + and − are used two separate wires are needed. Thus, for example, in a facial application where four channels are used this reduces the effective number of "wires" from 8 to 4. Further, the use of twin core leads means the confusion associated with collections of + and − leads can be avoided. Also, the electrode assembly can be sized for specific muscle groups and colour coded to make it easier for users to place the electrodes at the proper locations on the patient's skin.

The assembly according to the invention also fixes the distance between the electrodes, thereby better controlling the locus of the stimulation. The fact that the electrodes cannot be separated means that one cannot stimulate across sensitive structures, e.g. the neck or the orbit of the eye, which can be dangerous.

It will be understood that in more complex embodiments of the invention, the electrode assembly 10 may include more than two electrodes 18. It will also be understood that the electrodes 18 may be constructed other than as described. For example, each contact 15 could be fabricated from a single piece, which when pushed through the substrate 13 momentarily stretches the material before allowing the material to flex back to normal and retain the contact within the substrate 13. Further, the contacts 15 need not be fabricated entirely from metal, rather they could, for example, be fabricated from metal coated plastic which has the advantage of being lighter than an all-metal contact.

It will also be seen that the hydrogel layer 14 need not have an homogeneous electrical characteristic. It is possible to 'dope' the layer 14 in the region between the contacts 15 to increase the impedence of the layer laterally through the layer with or without the provision of a narrowed waist portion 12.

The invention is not limited to the embodiments described herein which may be modified or varied without departing from the scope of the invention.

What is claimed is:

1. An electrode assembly for application to a patient's skin, the assembly comprising an electrically insulating substrate bearing at least two spaced apart electrodes and an electrically conductive layer on the same side of the substrate as the electrodes, the layer covering the electrodes and extending continuously over the substrate between the electrodes and being applied to the patient's skin in use of the assembly, and the electrical impedance through the thickness of the layer in the region overlying each electrode being less than the electrical impedance between the electrodes laterally through the layer, wherein the assembly includes at least two spaced apart conductive members each having a base on the side of the substrate which bears the electrically conductive layer and an upstanding stud which passes through a hole in the substrate, and wherein each electrode is constituted solely by the base of a respective conductive member and the stud enables contact to be made to the respective electrode from the opposite side of the substrate.

2. A method of manufacturing an electrode assembly as claimed in claim 1, including the steps of providing a conductive layer removably adhered to a carrier layer, applying a substrate bearing a plurality of spaced apart electrodes to the electrically conductive layer so that the layer covers the electrodes, punching the substrate and conductive layer to define a plurality of electrode assemblies removably adhered to the carrier layer and each including at least two electrodes, and removing the electrode assemblies from the carrier layer.

3. An electrode assembly according to claim 1, wherein the said conductive member comprises the male part of a male/female connector, the connector having a female part with a base on the other side of the substrate to the base of the male part and an upstanding socket which snap engages over the stud, the part of the substrate surrounding the said hole being sandwiched between the bases of the male and female parts.

4. An electrode assembly according to claim 1 or 3, wherein the substrate is waisted between the two electrodes.

5. An electrode assembly according to claim 1 or 3, wherein the electrically conductive layer is a hydrogel layer.

* * * * *